(12) United States Patent
Curro

(10) Patent No.: US 6,198,018 B1
(45) Date of Patent: *Mar. 6, 2001

(54) ABSORBENT ARTICLE HAVING A BREATHABLE, FLUID IMPERVIOUS BACKSHEET

(75) Inventor: John J. Curro, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/241,245

(22) Filed: Feb. 1, 1999

Related U.S. Application Data

(63) Continuation of application No. 08/744,487, filed on Nov. 6, 1996, now Pat. No. 5,865,823.

(51) Int. Cl.[7] .................................................. A61F 13/15
(52) U.S. Cl. ................................................................ 604/367
(58) Field of Search .................................. 604/367, 378, 604/365, 370, 381, 385.1, 382, 384

(56) References Cited

U.S. PATENT DOCUMENTS

| | | | |
|---|---|---|---|
| 3,426,754 | 2/1969 | Bierenbaum | 128/156 |
| 3,651,014 | 3/1972 | Witsiepe | 260/75 R |
| 3,763,109 | 10/1973 | Witsiepe | 260/75 R |
| 3,766,146 | 10/1973 | Witsiepe | 260/75 R |
| 3,881,489 | 5/1975 | Hartwell | 128/287 |
| 3,904,706 | 9/1975 | Hoeschele | 260/858 |
| 3,989,867 | 11/1976 | Sisson | 428/132 |
| 4,014,341 | 3/1977 | Karami | 128/287 |
| 4,091,164 | 5/1978 | Schwarz | 428/404 |
| 4,116,892 | 9/1978 | Schwarz | 521/62 |
| 4,153,751 | 5/1979 | Schwarz | 428/304 |
| 4,289,832 | 9/1981 | Schwarz | 428/542 |
| 4,306,559 | 12/1981 | Nishizawa et al. | 128/287 |
| 4,324,246 | 4/1982 | Mullane et al. | 128/287 |
| 4,341,216 | 7/1982 | Obenour | 128/287 |
| 4,341,217 | 7/1982 | Ferguson et al. | 128/290 |
| 4,342,314 | 8/1982 | Radel et al. | 128/287 |
| 4,350,655 | 9/1982 | Hoge | 264/145 |
| 4,368,295 | 1/1983 | Newton et al. | 525/166 |
| 4,395,215 | 7/1983 | Bishop | 425/290 |
| 4,493,870 | 1/1985 | Vrouenraets et al. | 428/245 |
| 4,539,255 | 9/1985 | Sato et al. | 428/252 |
| 4,681,578 | 7/1987 | Anderson et al. | 604/385 |
| 4,681,793 | 7/1987 | Linman et al. | 428/138 |
| 4,698,372 | 10/1987 | Moss | 521/145 |
| 4,725,481 | 2/1988 | Ostapchenko | 428/213 |
| 4,747,991 | 5/1988 | Bishop | 264/504 |
| 4,761,324 | 8/1988 | Rautenberg et al. | 428/198 |
| 4,769,273 | 9/1988 | Hoeschele et al. | 428/215 |

(List continued on next page.)

FOREIGN PATENT DOCUMENTS

| | | |
|---|---|---|
| 0 560 630 B1 | 11/1999 | (EP) . |
| 2 024 100 | 1/1980 | (GB) . |
| WO 95/16746 | 6/1995 | (WO) . |
| WO 95/17867 | 7/1995 | (WO) . |

*Primary Examiner*—John G. Weiss
*Assistant Examiner*—David J. Cho
(74) *Attorney, Agent, or Firm*—Caroline Wei-Berk; Kevin D. Hogg; William Scott Andes

(57) ABSTRACT

A disposable absorbent article having a breathable fluid impervious backsheet. The disposable absorbent article preferably includes a fluid pervious topsheet, a breathable, fluid impervious backsheet secured to the topsheet, and an absorbent core disposed between the topsheet and the backsheet. The breathable, fluid impervious backsheet exhibits substantially zero dynamic fluid transmission when subjected to an impact energy of about 1000 joules/m$^2$, and exhibits a mass vapor transmission rate of at least about 2000 g/m$^2$/24 hr.

27 Claims, 4 Drawing Sheets

U.S. PATENT DOCUMENTS

| | | | |
|---|---|---|---|
| 4,777,073 | 10/1988 | Sheth | 428/155 |
| 4,795,454 | 1/1989 | Dragoo | 604/385.2 |
| 4,868,062 | 9/1989 | Hoeschele et al. | 428/423.1 |
| 4,872,871 | 10/1989 | Proxmire et al. | 604/394 |
| 4,887,602 | 12/1989 | O'Leary | 604/305.1 |
| 4,900,317 | 2/1990 | Buell | 604/370 |
| 4,908,026 | 3/1990 | Sukiennik et al. | 604/378 |
| 4,908,260 | 3/1990 | Dodia et al. | 428/215 |
| 4,923,650 | 5/1990 | Antoon, Jr. et al. | 264/41 |
| 4,935,287 | 6/1990 | Johnson et al. | 428/198 |
| 4,938,752 | 7/1990 | Vrouenraets et al. | 604/370 |
| 5,008,296 | 4/1991 | Antoon, Jr. et al. | 521/91 |
| 5,011,698 | 4/1991 | Antoon, Jr. et al. | 426/395 |
| 5,032,450 | 7/1991 | Rechlicz et al. | 428/196 |
| 5,036,551 | 8/1991 | Dailey et al. | 2/167 |
| 5,069,678 | 12/1991 | Yamamoto et al. | 604/385.1 |
| 5,085,654 | 2/1992 | Buell | 604/370 |
| 5,098,423 | 3/1992 | Pieniak et al. | 604/385.1 |
| 5,158,819 | 10/1992 | Goodman, Jr. et al. | 428/131 |
| 5,418,044 | 5/1995 | Mahler | 428/196 |
| 5,422,172 | 6/1995 | Wu | 428/230 |
| 5,445,874 | 8/1995 | Shehata | 428/252 |
| 5,447,783 | 9/1995 | Horn | 428/216 |
| 5,506,024 | 4/1996 | Flesher | 428/85 |
| 5,509,142 | 4/1996 | Connell et al. | 2/79 |
| 5,527,302 | 6/1996 | Endres et al. | 604/385.1 |
| 5,532,053 | 7/1996 | Mueller | 428/287 |
| 5,571,096 | 11/1996 | Dobrin et al. | 604/383 |
| 5,592,690 | 1/1997 | Wu | 2/67 |
| 5,614,302 | 3/1997 | Nance, Jr. | 442/286 |
| 5,786,412 | 7/1998 | Shah et al. | 524/264 |
| 5,789,065 | 8/1998 | Haffner et al. | 428/152 |
| 5,800,928 | 9/1998 | Fischer et al. | 428/500 |
| 5,865,823 * | 2/1999 | Curro | 604/367 |
| B1 4,636,207 | 11/1989 | Buell | 604/370 |

\* cited by examiner

ABSORBENT ARTICLE HAVING A BREATHABLE, FLUID IMPERVIOUS BACKSHEET

This is a continuation of application Ser. No. 08/744,487, filed on Nov. 6, 1996, now U.S. Pat. No. 5,865,823.

FIELD OF INVENTION

The present invention relates generally to disposable absorbent articles such as disposable diapers, incontinence briefs, incontinence undergarments, incontinence pads, feminine hygiene garments, training pants, pull-on garments, and the like and, more particularly, to disposable absorbent articles having a breathable, fluid impervious backsheet.

BACKGROUND OF THE INVENTION

Infants and other incontinent individuals wear disposable absorbent articles such as diapers to receive and contain urine and other body exudates. Absorbent articles function both to contain the discharged materials and to isolate these materials from the body of the wearer and from the wearer's garments and bed clothing. Disposable absorbent articles having many different basic designs are known to the art. It is also known that the exterior of disposable diapers can be covered with a flexible, fluid and vapor impervious sheet to prevent any absorbed fluid from passing through the diaper and soiling adjacent articles such as clothing, bedding and the like. These outer covers, generally referred to as backsheets, are often constructed from fluid impervious films such as polyethylene. Although such backsheets do prevent fluid from passing through the diaper, they also can make the diaper feel hot and uncomfortable to wear because of their impermeability to air and/or moisture.

Backsheets which are pervious to vapor are generally known as breathable backsheets and have been described in the art. In general, these backsheets are intended to allow the passage of vapor through them while retarding, at least to a degree, the passage of fluid. For example, U.S. Pat. No. 3,156,242 issued to Crowe, Jr. on Nov. 10, 1964 teaches the use of a microporous film as a breathable backsheet. U.S. Pat. No. 3,881,489, issued to Hartwell on May 6, 1975, teaches a breathable backsheet comprising in combination two layers, the first of which is a low void volume perforated thermoplastic film and the second of which is a porous high void volume hydrophobic tissue. U.S. Pat. No. 3,989,867 issued to Sisson on Nov. 2, 1976 teaches a breathable backsheet provided with tapered hollowed bosses which prevent the passage of fluids while allowing vapors to pass readily therethrough.

While these backsheets do provide improvements over the commonly practiced impermeable backsheets of the prior art, they have been found to not be sufficiently fluid impervious when subjected to normal usage conditions. For example, when used as a backsheet on a disposable diaper, the backsheets may permit the transmission of urine upon impact from an infant sitting down. This ability of a fluid to be forced through such materials results in the unwanted transmission of urine waste through the diaper backsheet.

Therefore, it is an object of the present invention to provide a disposable absorbent article backsheet having good containment characteristics while being breathable to ensure comfort for the wearer.

It is yet another object of this invention to provide a disposable absorbent article having a breathable backsheet having good containment characteristics when subjected to normal usage conditions.

These and other objects of the present invention will be more readily apparent when considered in reference to the following description and when taken in conjunction with the accompanying drawings.

SUMMARY OF THE INVENTION

The present invention is directed to disposable absorbent articles, such as disposable diapers, having a backsheet at least a portion of which is breathable and fluid impervious. The disposable absorbent article preferably comprises a containment assembly including a fluid pervious topsheet, a backsheet joined to the topsheet, and an absorbent core disposed between the topsheet and the backsheet. The absorbent core has a pair of opposing longitudinal edges, an inner surface and an outer surface. In some embodiments at least a portion of the backsheet exhibits substantially zero dynamic fluid transmission when subjected to an impact energy of about 1000 joules/m$^2$ and will also exhibit a mass vapor transmission rate of at least about 2000 g/m$^2$/24 hr. In other embodiments the entire backsheet will exhibit substantially zero dynamic fluid transmission when subjected to an impact energy of about 1000 joules/m$^2$ and will also exhibit a mass vapor transmission rate of at least about 2000 g/m$^2$/24 hr.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form it coordinated entity so that they do not require separate manipulative parts like a separate holder and liner.

Figure 1:
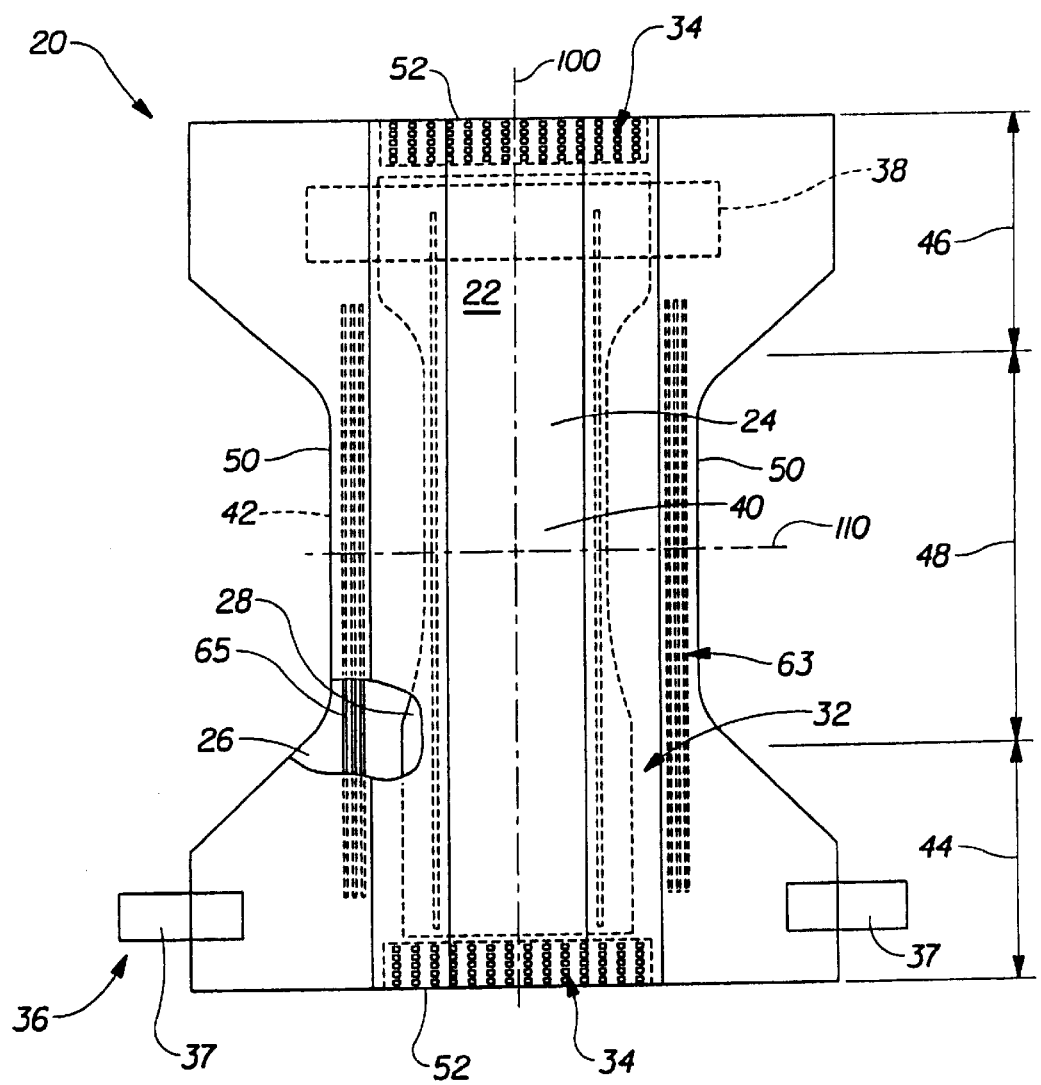
FIG. 1 is a plan view of a disposable diaper embodiment of the present invention having portions cut away to reveal underlying structure, the inner surface of the diaper is facing the viewer.

A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinence briefs, incontinence undergarments, diaper holders and liners, feminine hygiene garments, training pants, pull-on garments, and the like.

FIG. 1 is a plan view of the diaper 20 of the present invention in its flat-out, uncontracted state (i.e., with elastic induced contraction pulled out) with portions of the structure being cut-away to more clearly show the construction of the diaper 20. As shown in FIG. 1, the diaper 20 preferably comprises a containment assembly 22 comprising a topsheet 24; a backsheet 26 joined to the topsheet; and an absorbent core 28 positioned between the topsheet 24 and the backsheet 26. The absorbent core 28 has a pair of opposing longitudinal edges, an inner surface and an outer surface. The diaper preferably further comprises elastic leg features 32; elastic waist features 34; and a fastening system 36 preferably comprising a pair of securement members 37 and a landing member 38.

The diaper 20 is shown in FIG. 1 with the portion of the diaper 20 which faces the wearer, the inner surface 40, facing the viewer. The diaper 20 is shown in FIG. 1 to have an inner surface 40 (facing the viewer in FIG. 1), an outer surface 42 opposed to the inner surface 40, a rear or back waist region 44, a front waist region 46 opposed to the rear waist region 44, a crotch region 48 positioned between the rear waist region 44 and the front waist region 46, and a periphery which is defined by the outer perimeter or edges of the diaper 20 in which the longitudinal or side edges are designated 50 and the end edges are designated 52. The inner surface 40 of the diaper 20 comprises that portion of the diaper 20 which is positioned adjacent to the wearer's body during use (i.e., the inner surface 40 generally is formed by at least a portion of the topsheet 24 and other components joined to the topsheet 24). The outer surface 42 comprises that portion of the diaper 20 which is positioned away from the wearer's body (i.e., the outer surface 42 is generally formed by at least a portion of the backsheet 26 and other components joined to this backsheet 26). As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. The rear waist region 44 and the front waist region 46 extend from the end edges 52 of the periphery to the crotch region 48.

The diaper 20 also has two centerlines, a longitudinal centerline 100 and a transverse centerline 110. The term "longitudinal", as used herein, refers to a line, axis, or direction in the plane of the diaper 20 that is generally aligned with (e.g. approximately parallel with) a vertical plane which bisects a standing wearer into left and right halves when the diaper 20 is worn. The terms "transverse" and "lateral", as used herein, are interchangeable and refer to a line, axis or direction which lies within the plane of the diaper that is generally perpendicular to the longitudinal direction (which divides the wearer into front and back body halves).

Figure 1A:
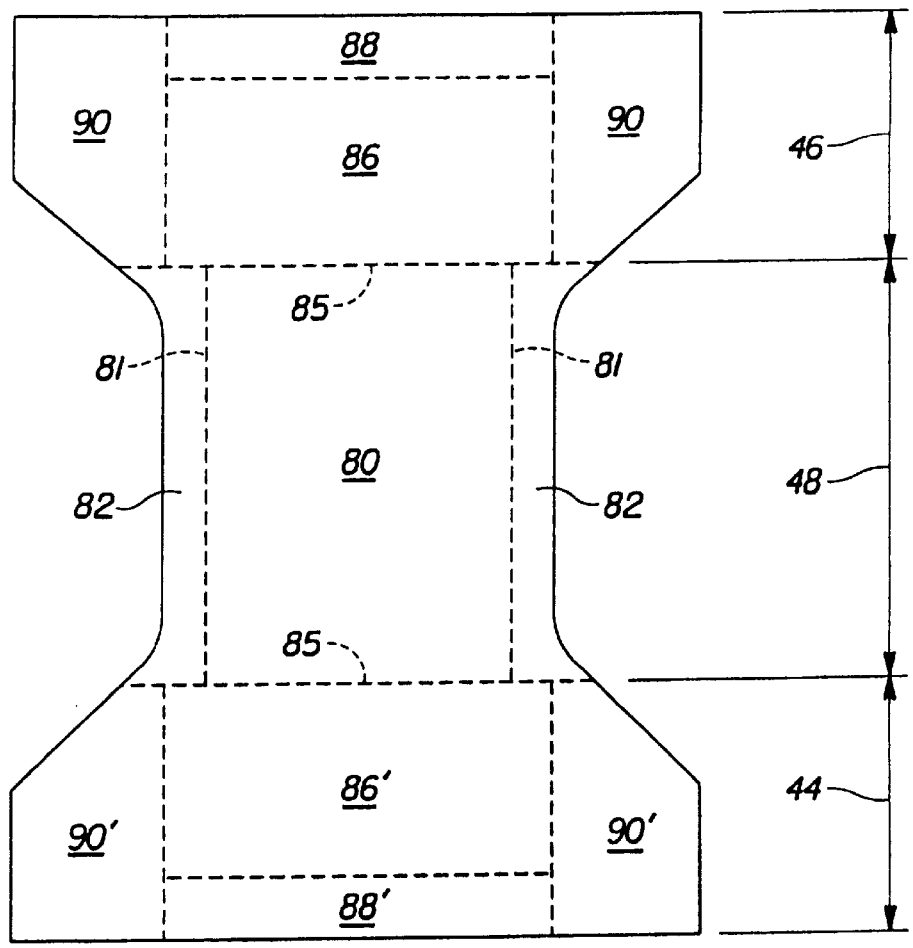
FIG. 1A is a simplified plan view of the disposable diaper of the present invention in its flat uncontracted condition showing the various panels or zones of the diaper.

FIG. 1A shows a simplified plan view of the diaper 20 of FIG. 1 depicting the various panels and their positioning with respect to each other. The term "panel" is used herein to denote an area or element of the diaper. (While a panel is typically a distinct area or element, a panel may coincide (functionally correspond) somewhat with an adjacent panel.) The diaper 20 has a crotch region 48 comprising a main panel 80 and a pair of leg panels 82; a front waist region 46 comprising a central panel comprising a medial panel 86 and a waistband panel 88, and side panels 90; and a rear waist region 44 comprising a central panel comprising a medial panel 86' and a waistband panel 88', and side panels 90'. The main panel 80 is the portion of the diaper 20 from which the other panels emanate. The absorbent core is generally positioned within the main panel 80 since exudates are typically discharged in this region of the diaper although the absorbent core will also likely extend into the medial panels 86 and 86'. A leg panel 82 extends generally laterally outwardly front and along each side edge 81 of the main panel 80. Each leg panel 82 generally forms at least a portion of the elastic leg feature. In the front waist region 46, the medial panel 86 of the central panel extends generally longitudinally outwardly from and along the lateral edge 85 of the main panel 80. The waistband panel 88 extends generally longitudinally outwardly from and along the medial panel 86. The side panels 90 each extend generally laterally outwardly from and along the central panel. In the rear waist region 44, the medial panel 86' of the central panel extends generally longitudinally outwardly from and along the lateral edge 85 of the main panel 80. The waistband panel 88' extends generally longitudinally outwardly from and along the medial panel 86'. The side panels 90' each extend generally laterally outwardly from and along the central panel.

Referring again to FIG. 1 the containment assembly 22 of the diaper 20 is shown as comprising the main body (chassis) of the diaper 20. The containment assembly 22 preferably comprises a topsheet 24, a backsheet 26 and an absorbent core 28 having a pair of opposing longitudinal edges, an inner surface, an outer surface. The inner surface of the absorbent core generally faces the body of the wearer while the outer surface generally faces away from the body of the wearer. When the absorbent article comprises a separate holder and a liner, the containment assembly 22 generally comprises the holder and the liner (i.e., the containment assembly 22 comprises one or more layers of material to define the holder while the liner comprises an absorbent composite such as a topsheet, a backsheet, and an absorbent core.) For unitary absorbent articles, the containment assembly 22 preferably comprises the topsheet 24, the backsheet 26 and the absorbent core 28 of the diaper with other features added to form the composite diaper structure.

FIG. 1 shows a preferred embodiment of the containment assembly 22 in which the topsheet 24 and the backsheet 26 have length and width dimensions generally larger than those of the absorbent core 28. The topsheet 24 and the backsheet 26 extend beyond the edges of the absorbent core 28 to thereby form the periphery of the diaper 20. While the topsheet 24, the backsheet 26, and the absorbent core 28 may be assembled in a variety of well known configurations, exemplary containment assembly configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992; each of which is incorporated herein by reference.

In the embodiment shown in FIG. 1, the backsheet 26 preferably comprises a continuous sheet or layer which defines the front waist region 46, the rear waist region 44, and the crotch region 48. As used herein, the term "layer" does not necessarily limit the element to a single strata of material in that a layer may actually comprise laminates or combinations of sheets or webs of the requisite types of materials. The backsheet 26 has an inner surface and an opposed outer surface. The inner surface is that portion of the backsheet 26 which is positioned adjacent the absorbent core. The outer surface of the backsheet 26 corresponds to the outer surface 42 of the diaper 20. Since the backsheet 26 preferably defines the front waist region 46, the rear waist 44, and the crotch region 48, the backsheet 26 also has corresponding regions and panels as previously defined. (For simplicity, these regions and panels are denoted in the drawings by the same reference numerals as the corresponding diaper regions and panels as shown in FIG. 1A)

In the embodiment shown in FIG. 1, the absorbent core is positioned in the main panel 80, since exudates are typically discharged in this region and extends into the medial panels 86 and 86'. In the embodiment shown in FIG. 1, the absorbent core does not extend into the leg panels 82, the waistband panels 88 and 88', or the side panels 90 and 90'. In other embodiments, the absorbent core may extend into all or some of the leg panels 82, the waistband panels 88 and 88', and the side panels 90 and 90'.

The backsheet 26 of the present invention is that portion of the diaper 20 which is generally positioned away from the wearer's skin and which prevents the exudates absorbed and contained in the absorbent core 28 from wetting articles which contact the diaper 20 such as bedsheets and undergarments. Thus, the backsheet 26 is impervious to fluids (e.g., urine). In addition to being fluid impervious, the backsheet 26 is also breathable. For disposable diapers, breathability has been found to be critical to performance especially in hot and humid conditions. When an absorbent article is positioned on a wearer, the skin is occluded by the materials making up the absorbent article. This occlusion of the skin, especially in hot and humid conditions, prevents evaporation and the resulting cooling of the occluded area. The resultant perspiration raises the relative humidity of air inside of the absorbent article resulting in less comfort for the wearer and perceived negative benefits by caregivers.

It has been found that the moisture vapor transmission rate of the backsheet is important in reducing the incidence of heat rash and other skin problems associated with high heat and humidity conditions. In order to reduce humidity and heat buildup within the disposable diaper, it has been found that at least a portion of the backsheet 26, and more preferably the entire backsheet 26, should have a mass vapor transmission rate of at least about 2000 g/m$^2$/24 hr., more preferably at least about 2500 g/m$^2$/24 hr., and most preferably at least about 3000 g/m$^2$/24 hr. Backsheets of the present invention may have even higher mass vapor transmission rates, e.g., mass vapor transmission rates of at least about 4000 g/m$^2$/24 hr. or greater.

The moisture vapor transmission rate is measured by the method set forth below. A known amount of CaCl$_2$ is put into a flanged cup. A sample material is placed on top of the cup and held securely by a retaining ring and gasket. The assembly is then weighed and recorded as the initial weight. The assembly is placed in a constant temperature (40° C.) and humidity (75% RH) chamber for five (5) hours. The assembly is then removed from the chamber and allowed to equilibrate for at least 30 minutes at the temperature of the room where the balance is located. The assembly is then weighed and recorded as the final weight. The mass vapor transmission rate (MVTR) is calculated and expressed in g/m$^2$/24 hr. using the following formula:

$$MVTR = \frac{(\text{final weight} - \text{initial weight}) \times 24.0}{\text{area of sample in meters} \times 5.0 \,(\text{time in chamber})}$$

Conventional diapers have attempted to use breathable materials to reduce the humidity within the diaper. However, it has been found that these materials have not been sufficiently fluid impervious when subjected to the normal usage conditions, e.g., mechanical impact from an infant sitting down. The ability of a fluid to be forced through such materials during normal usage conditions results in current breathable products exhibiting unwanted transmission of urine waste through the backsheet. Therefore, it would be desirable to provide a backsheet for use on a disposable absorbent article such as a disposable diaper which is not only breathable, i.e., exhibits a MVTR at least about 2000 g/m$^2$/24 hr., but also exhibits substantially zero dynamic fluid transmission when subjected to normal usage conditions, such as when an infant sits down. As used herein, "substantially zero dynamic fluid transmission" includes any measured value less than 0.5 g/m$^2$ when subjecting a material to the dynamic fluid impact test method set forth below.

The dynamic fluid impact test method set forth below is designed to mimic the energy per area that an infant imparts to a diaper backsheet when abruptly going from a standing to a sitting position. While other common infant movements and activities, (e.g., rolling on the ground), may also cause leakage by transmitting urine through the diaper backsheet, the sitting action provides a clear mechanical interaction which can be analyzed to gain a quantitative understanding of the actual impact energies involved in typical diaper usage conditions.

Figure 2:
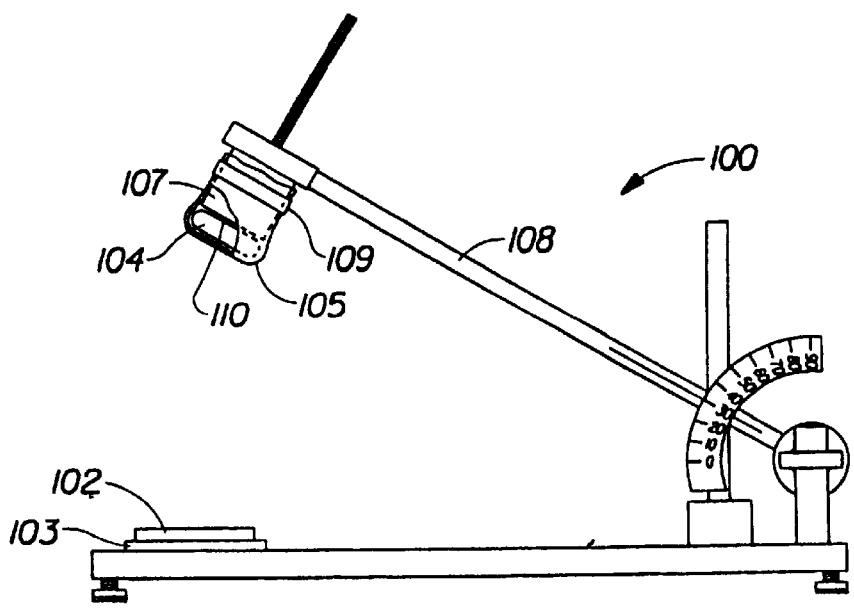
FIG. 2 is a simplified illustration of an apparatus used for determining the fluid impact value.

The dynamic fluid impact test method utilizes the apparatus 100 shown in FIG. 2. An absorption material 102 weighed to the nearest 0.0001 gram is placed directly on top of the energy absorbing impact pad 103. To this purpose, the absorption material 102 can comprise a No. 2 filter paper available from Whatman Laboratory Division, Distributed by VWR Scientific of Cleveland, Ohio. The absorption material should be able to absorb and retain the simulated urine which passes through the backsheet material being tested. The energy absorbing impact pad 103 is a carbon black filled cross linked rubber foam. The 5 inch by 5 inch square impact pad has a density of 0.1132 gm/cm$^3$ and a thickness of 0.3125 inches. The impact pad 103 has a Durometer Value of A/30/15 according to ASTM 2240-91.

A circular absorbent core material 104 measuring 0.0635 meters (2.5 inches) in diameter is weighed. To this purpose, the absorbent core material can comprise individualized, crosslinked wood pulp cellulosic fibers as described in U.S. Pat. No. 5,137,537 issued to Herron et al. on Aug. 11, 1992. The absorbent core has a basis weight of about 228 g/m$^2$. The absorbent core material is then is loaded with simulated urine to about ten (10) times its dry weight. This represents an absorbent core sufficiently loaded with urine. The absorbent core material should be able to hold a sufficient amount of simulated urine, e.g., at least about ten times its dry weight. Accordingly, other absorbent core materials currently used in commercial diapers may also be used as the absorbent core material. The simulated urine can comprise distilled water.

A section of the backsheet material 105 to be tested is placed face down with the outside surface on a clean and dry tabletop. The loaded core material 104 is placed directly in the center of the backsheet material 105. The backsheet/core arrangement is then secured to the impact portion 107 of the impact arm 108 with a rubber band 109. The backsheet/core arrangement is positioned such that the core 104 is adjacent the bottom surface 110 of the impact portion 107. The impact arm 108 is raised to a desired impact angle to provide the desired impact energy. The impact arm 108 is then dropped and a stop watch is activated on impact. The arm then rests on the filter paper 102 for ten seconds. The impact arm 108 is then raised and the filter paper 102 is removed and placed on a digital scale. The mass of the wet filter paper is then recorded at the three minute mark. The dynamic fluid transmission value (DFTV) is calculated and expressed in g/m² using the following formula:

$$DFTV = \frac{\text{mass of the wet filter paper (grams)} - \text{mass of the dry filter paper (grams)}}{\text{impact area (m}^2\text{)}}$$

The impact area, expressed in m², is the area of the bottom surface 110 of the impact portion 107. The impact area is 0.00317 m². The absorbent core material 104 should have an area slightly larger than that of the impact area of the surface 110.

In addition to exhibiting a mass vapor transmission rate of at least about 2000 g/m²/24 hr., suitable materials for the backsheet will also exhibit substantially zero dynamic fluid transmission when subjected to an impact energy of about 1000 joules/m². Preferably, the backsheets of the present invention while exhibiting a mass vapor transmission rate of at least about 2000 g/m²/24 hr. will also exhibit substantially zero dynamic fluid transmission when subjected to impact energies of about 2000 joules/m², about 3000 joules/m², and about 4000 joules/m². Backsheets of the present invention may exhibit substantially zero dynamic fluid transmission when subjected to even higher impact energies, e.g., impact energies of at least about 5000 joules/m² or greater.

Suitable backsheet materials which exhibit substantially zero dynamic fluid transmission when subjected to an impact energy of about 1000 joules/m² and also exhibit a mass vapor transmission rate of at least about 2000 g/m²/24 hr. include a single layer monolithic film capable of passing sufficient moisture vapor such as a polyester based film or may comprise two or more layers such as a polyester-based film extrusion coated onto a nonwoven web.

The following materials were subjected to the mass vapor transmission rate test and the dynamic fluid impact test described above.

Sample A—Exxon Exxair XFB-100W available from Exxon Chemical Company of Buffalo Grove, Ill.

Sample B—DuPont Hytrel Film blend #P18-3097 available from Clopay Corporation, Cincinnati, Ohio.

Sample C—DuPont Hytrel Film blend #P18-3096 available from Clopay Corporation, Cincinnati, Ohio.

Sample D—Breathable test film supplied by Minnesota Mining and Manufacturing Company of Minneapolis-Saint Paul, Minn. The results of the mass vapor transmission rate test and the dynamic fluid impact test are set forth in Table 1.

TABLE 1

Mass Vapor Transmission Rate (MVTR) and Dynamic Fluid Transmission Value (DFTV)

| Sample | MVTR in g/m²/24 hr. | DFTV in g/m² at 1000 joules/m² |
|---|---|---|
| A | 5157 | 3.96 |
| B | 2400 | 0.28 |
| C | 3860 | 0.40 |
| D | 5242 | 1.22 |

As can be seen from Table 1, Samples B and C exhibited substantially zero dynamic fluid transmission when subjected to an impact energy of 1000 joules/m² and also exhibited a mass vapor transmission rate of at least about 2000 g/m²/24 hr. Samples B and C would thus be suitable for use as a backsheet on a disposable diaper as they would be breathable and sufficiently fluid impervious when subjected to normal usage conditions. Samples A and D were sufficiently breathable, (i.e., they had mass vapor transmission rates of at least about 2000 /m²/24 hr.), however, they exhibited an unacceptable degree of dynamic fluid transmission when subjected to an impact energy of 1000 joules/m².

Additionally suitable backsheet materials would be those that exhibit substantially zero dynamic fluid transmission when subjected to an impact energy of about 1000 joules/m² and also exhibit a mass vapor transmission rate of at least about 2000 g/m²/24 hr. via spacial separation of these key properties within the backsheet structure. For example, selectively vented or apertured backsheets may be utilized if the vented portions have a mass vapor transmission rate of at least about 2000g/m²/24 hr. and also exhibit substantially zero dynamic fluid transmission when subjected to an impact energy of about 1000 joules/m².

The backsheet 26 is preferably positioned adjacent the outer surface of the absorbent core 28 and is preferably-joined thereto by any suitable attachment means known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. An example of a suitable attachment means comprising an open pattern network of filaments of adhesive is disclosed in U.S. Pat. No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

Embodiments of the present invention are also contemplated wherein the absorbent core is not joined to the backsheet 26, and/or the topsheet 24 in order to provide greater extensibility in the front waist region 46 and the rear waist region 44.

The absorbent core 28 may be any absorbent member which is generally compressible, conformable, non-irritating to the wearer's skin, and capable of absorbing and retaining fluids such as urine and other certain body exudates. All shown in FIG. 1, the absorbent core 28 has a garment-facing side, a body-facing side, a pair of side edges, and a pair of waist edges. The absorbent core 28 may be manufactured in a wide variety of sizes and shapes (e.g., rectangular, hourglass, "T"-shaped, asymmetric, etc.) and from a wide variety of fluid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 28 may vary (e.g., the absorbent core may have varying caliper zones, a hydrophilic gradient, a superabsorbent gradient, or lower average density and lower average basis weight acquisition zones; or may comprise one or more layers or structures). Further, the size and absorbent capacity of the absorbent core 28 may also be varied to accommodate wearers ranging from infants through adults. However, the total absorbent capacity of the absorbent core 28 should be compatible with the design loading and the intended use of the diaper 20.

One embodiment of the diaper 20 has an asymmetric, modified T-shaped absorbent core 28 having ears in the front waist region but a generally rectangular shape in the rear waist region. Exemplary absorbent structures for use as the absorbent core 28 of the present invention that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference.

The topsheet 24 is preferably positioned adjacent the inner surface of the absorbent core 28 and is preferably joined thereto and to the backsheet 26 by attachment means (not shown) such as those well known in the art. Suitable attachment means are described with respect to joining the backsheet 26 to the absorbent core 28. In a preferred embodiment of the present invention, the topsheet 24 and the backsheet 26 are joined directly to each other in the diaper periphery and are indirectly joined together by directly joining them to the absorbent core 28 by any suitable attachment means.

The topsheet 24 is preferably compliant, soft feeling, and non-irritating to the wearer's skin. Further, the topsheet 24 is preferably fluid pervious permitting fluids (e.g., urine) to readily penetrate through its thickness. A suitable topsheet 24 may be manufactured from a wide range of materials such as woven and nonwoven materials; polymeric materials such as apertured formed thermoplastic films,, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. The topsheet 24 is preferably made of a hydrophobic material to isolate the wearer's skin from fluids which have passed through the topsheet 24 and are contained in the absorbent core 28 (i.e. to prevent rewet). If the topsheet 24 is made of a hydrophobic material, at least the upper surface of the topsheet 24 is treated to be hydrophilic so that fluids will transfer through the topsheet more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein.

An alternative preferred topsheet comprises an apertured formed film. Apertured formed films are preferred for the topsheet because they are pervious to body exudates and yet non-absorbent and have a reduced tendency to allow fluids to pass back through and rewet the wearer's skin. Thus, the surface of the formed film which is in contact with the body remains dry, thereby reducing body soiling and creating a more comfortable feel for the wearer. Suitable formed films are described. in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents are incorporated herein by reference.

It may also be desirable to provide the disposable article of the present invention with extensibility or elasticity in all or a portion of the side panels 90. (As used herein, the term "extensible" refers to materials that are capable of extending in at least one direction to a certain degree without undue rupture. The terms "elasticity" and "elastically extensible" refer to extensible materials that have the ability to return to approximately their original dimensions after the force that extended the material is removed. As used herein, any material or element described as "extensible" may also be elastically extensible unless otherwise provided.) Extensible side panels 90 provide a more comfortable and contouring fit by initially) conformably fitting the diaper to the wearer and sustaining this fit throughout the time of wear well passed when the diaper has been loaded with exudates since the side panels allow the sides of the diaper to expand and contract. Extensible side panels 90 further provide more effective application of the diaper 20 since even if the diaperer pulls one side panel 30 farther than the other during the application (asymmetrically), the diaper 20 will "self-adjust" during wear. While the extensible side panels 90 may be constructed in a number of configurations, examples of diapers with extensible side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; and in U.S. Pat. No. 5,151,092 issued to Buell et al. on Sep. 29, 1992; each of which are incorporated herein by reference.

The extensible side panels, or any other elements of the diaper 20 in which extensibility or elasticity is desirable such as the waistbands may comprise materials that have been "prestrained", or "mechanically prestrained" (i.e., subjected to some degree of localized pattern mechanical stretching to permanently elongate the material), or structural elastic-like webs, as described in U.S. Pat. No. 5,518,801 issued to Chappell et al. on May 21, 1996.

As disclosed in Chappell et al., such webs can be described as an extensible material which includes a strainable network of contiguous, distinct and dissimilar regions. The network includes at least a pair of first regions, a second region between said first regions, and a transitional region which is at the interface between each first region and the second region, the transition region generally exhibiting complex combinations of the behavior of both the first and second regions. The first regions are configured so that they will exhibit resistive forces in response to an applied axial elongation in a direction parallel to a predetermined first axis in a first direction before a substantial portion of the second region develops significant resistive forces to the applied elongation. The first regions each have a surface-pathlength as measured generally parallel to the predetermined first axis while the material is in an untensioned condition. The second region has a surface-pathlength which is greater than that of each of the first regions as measured generally parallel to the predetermined first axis while the material is in an untensioned condition, and preferably includes one or more raised rib-like elements which extend beyond the plane of the first regions and have an axis substantially perpendicular to the predetermined first axis. The materials may be prestrained using deep embossing techniques as are known in the art. Alternatively, the materials may be prestrained by directing the material through an incremental mechanical stretching system as described in U.S. Pat. No. 5,330,458 issued to Buell et al., on Jul. 19, 1994. The materials are then allowed to return to their substantially untensioned condition, thus forming a zero strain stretch material that is extensible, at least up to the point of initial stretching. Examples of zero strain materials are disclosed in U.S. Pat. No. 2,075,189 issued to Galligan on Mar. 30, 1937; U.S. Pat. No. 3,025,199 issued to Harwood on Mar. 13, 1962; U.S. Pat. Nos. 4,107,364 and 4,209,563 issued to Sisson on Aug. 15, 1978 and Jun. 24, 1980, respectively; U.S. Pat. No. 4,834,741 issued to Sabee on May 30, 1989; and U.S. Pat. No. 5,151,092 issued to Buell et al., on Sep. 29, 1992. All of the above referenced patents are hereby incorporated by reference.

The diaper 20 preferably further comprises elastic leg features 32 for providing improved containment of fluids and other body exudates. Each elastic leg feature 32 may comprise several different embodiments for reducing the leakage of body exudates in the leg panels 82 (the elastic leg feature can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987; and U.S. Pat. No. 4,795,454 entitled "Absorbent Article Having Leakage-Resistant Dual Cuffs" issued to Dragoo on Jan. 3, 1989, describe disposable diapers having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinence garment having side-edge-leakage-guard gutters configured to contain free fluids within the garment. Each of these patents are incorporated herein by reference.

While each elastic leg feature 32 may be configured so as to be similar to any of the leg bands, side flaps, barrier cuffs, or elastic cuffs described above, it is preferred that each elastic leg feature 32 comprise at least an inner barrier cuff comprising a barrier flap and a spacing element such as described in the above-referenced U.S. Pat. No. 4,909,803. In a preferred embodiment, the elastic leg feature 32 additionally comprises an elastic gasketing cuff 63 with one or more elastic strands 65, positioned outboard of the barrier cuff such as described in the above-referred U.S. Pat. No. 4,695,278.

The diaper 20 preferably further comprises an elastic waist feature 34 that provides improved fit and containment. The elastic waist feature 34 is that portion or zone of the diaper 20 which is intended to elastically expand and contract to dynamically fit the wearer's waist. The elastic waist feature 34 preferably extends longitudinally outwardly from at least one of the waist edges of the absorbent core 28 and generally forms at least a portion of the end edge of the diaper 20. Disposable diapers are generally constructed so as to have two elasticized waistbands, one positioned in the rear waist region and one positioned in the front waist region, although diapers can be constructed with a single elasticized waistband. Further, while the elastic waist feature 34 or any of its constituent elements can comprise a separate element affixed to the diaper 20, the elastic waist feature 34 may be constructed as an extension of other elements of the diaper such as the backsheet 26 or the topsheet 24, preferably both the backsheet 26 and the topsheet 24. Embodiments are also contemplated wherein the elastic waist feature 34 comprises apertures, as described above, to provide breathability in the waist regions. The elastic waist feature 34 may be constructed in a number of different configurations including those described in U.S. Pat. No. 4,515,595 entitled "Disposable Diapers with Elastically Contractible Waistbands" issued to Kievit et al. on May 7, 1985 and the above referenced U.S. Pat. No. 5,151,092 issued to Buell; each of these references being incorporated herein by reference.

The diaper 20 also comprises a fastening system 36 which forms a side closure which maintains the rear waist region 44 and the front waist region 46 in an overlapping configuration such that lateral tensions are maintained around the circumference of the diaper to maintain the diaper on the wearer. Exemplary fastening systems are disclosed in U.S. Pat. No. 3,848,594 issued to Buell on Nov. 19, 1974; U.S. Pat. No: 4,662,875 issued to Hirotsu and Robertson on May 5, 1987; U.S. Pat. No. 4,869,724 issued to Scripps on Sep. 26, 1989, U.S. Pat. No. 4,846,815 issued to Scripps on Jul. 11, 1989; U.S. Pat. No. 4,894,060 issued to Nestegard on Jan. 16, 1990; U.S. Pat. No. 4,946,527 issued to Battrelt on Aug. 7, 1990; and U.S. Pat. No. 5,326,612 entitled "Nonwoven Female Component For Refastenable Fastening Device And Method of Making the Same" issued to David J. K. Goulait on Jul. 5, 1994. Each of these patents are incorporated herein by reference.

Figure 3:
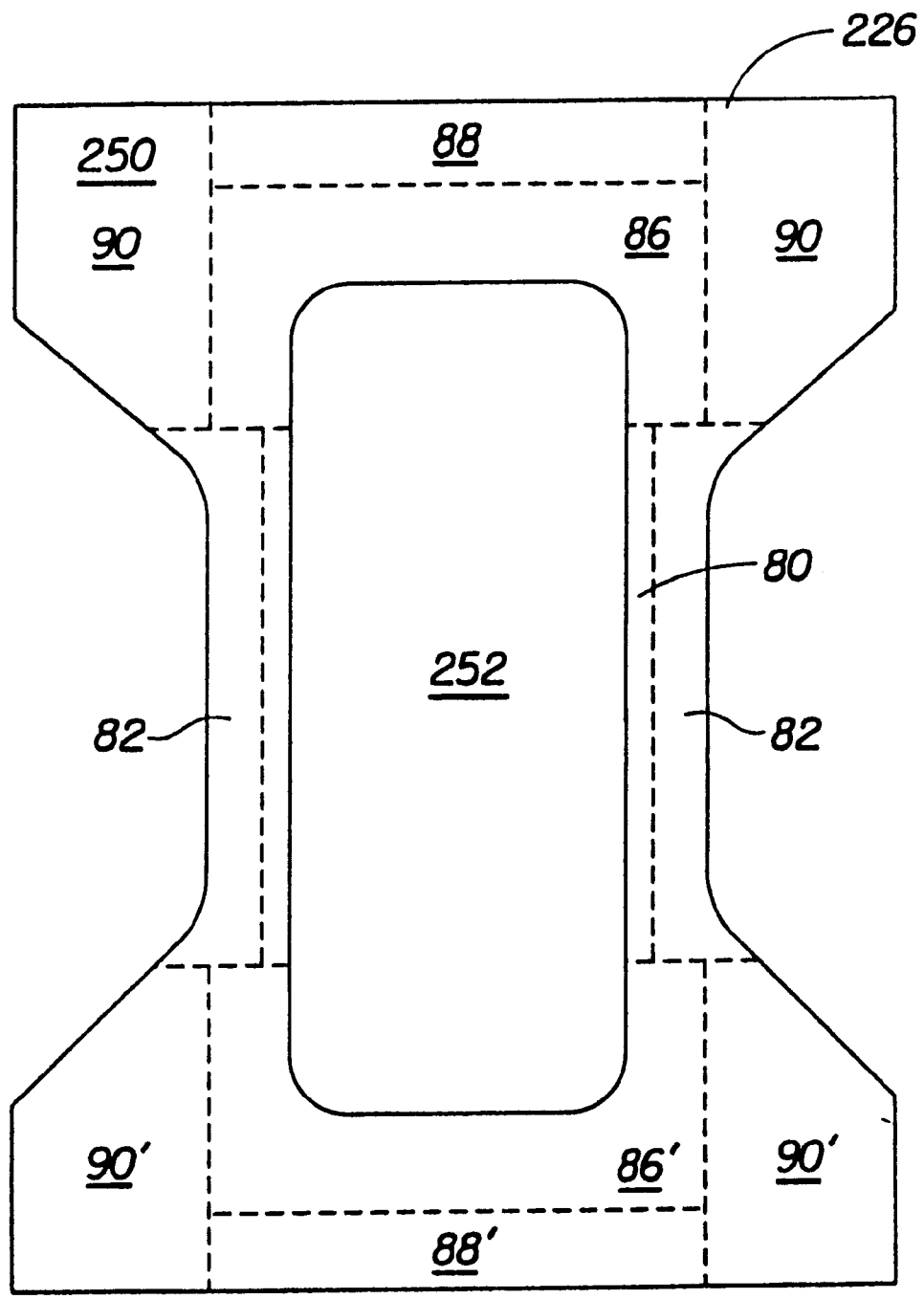
FIG. 3 is a plan view of another embodiment of a diaper backsheet of the present invention.

FIG. 3 shows a plan view of an alternative embodiment of the diaper backsheet of the present invention, with the portion of the backsheet positioned adjacent to the absorbent core facing the viewer. As shown in FIG. 3, the backsheet 226 comprises two layers 250 and 252. Layers 250 and 252 may be secured together by any suitable attachment means known in the art. In this embodiment, layer 250 forms the outer surface of the diaper and layer 252 is positioned adjacent to the absorbent core. Since layer 250 is that portion of the backsheet 226 which will come into contact with the wearer's skin, layer 250 is preferably soft and comprises a nonwoven web. In addition to being soft, layer 250 is preferably breathable. Layer 250 preferably exhibits a mass vapor transmission rate of at least about 2000 $g/m^2/24$ hr., more preferably at least about 2500 $g/m^2/24$ hr., and most preferably at least about 3000 $g/m^2/24$ hr. Layer 250 may have a higher mass vapor transmission rate, e.g., mass vapor transmission rate of at least about 4000 $g/m^2/24$ hr. or greater. Since layer 250 does not need to prevent leakage of exudates absorbed and contained within the absorbent core, selection of materials that provide the desired softness and breathability is quite extensive. Suitable materials include, but are not limited to, nonwoven webs such as spunbond webs, meltblown webs, carded webs and the like. The nonwoven webs for layer 250 may comprise synthetic fibers, natural fibers, multi-component fibers such as bi-component fibers, or mixtures and blends thereof.

Layer 252 is the portion of the backsheet 226 which will prevent the exudates absorbed and contained in the absorbent core from wetting articles which contact the diaper. In order to protect the user against unwanted leakage of exudates absorbed and contained within the absorbent core layer 252 should have width and length dimensions greater than those of the absorbent core. If layer 252 is not large enough exudates absorbed and contained in the absorbent core may find their way through the outer layer 250 during normal usage conditions. In the embodiment shown in FIG. 3, the absorbent core is preferably positioned in the main panel 80 and extends into the medial panels 86 and 86'. Accordingly, layer 252 is positioned within the main panel 80 and extends into the medial panels 86 and 86'. Layer 252 has length and width dimensions at least as large as those of the absorbent core and preferably greater than those of the absorbent core. If desired, layer 252 may extend beyond the main panel 80 and the medial panels 86 and 86' to into the leg panels 82, the waistband panels 88 and 88', and the side panels 90 and 90'. In addition, layer 252 may extend laterally and longitudinally outwardly from the main panel 80 to form portions of the periphery of the disposable diaper.

While layer 250 provides a substantial amount of breathability for the diaper, layer 252 is also breathable providing additional comfort for the wearer. As noted above, breathability has been found to be critical to the performance of the diaper. To this end, layer 252 should substantially exhibit zero dynamic fluid transmission when subjected to an impact energy of about 1000 joules/$m^2$ and exhibit a mass vapor transmission rate of at least about 2000 $g/m^2/24$ hr. Preferably, layer 252 while exhibiting a mass vapor transmission rate of at least about 2000 $g/m^2/24$ hr. will also exhibit substantially zero dynamic fluid transmission when subjected to impact energies of about 2000 joules/$m^2$, about 3000 joules/$m^2$, and about 4000 joules/$m^2$. The innermost layer 252 may exhibit substantially zero dynamic fluid transmission when subjected to even higher impact energies, e.g., impact energies of at least about 5000 joules/$m^2$ or greater.

Figure 4:
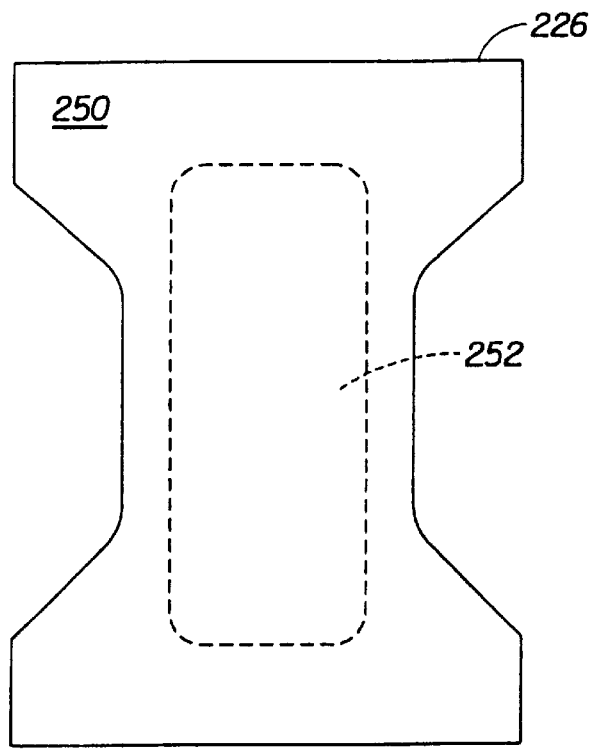
FIG. 4 is a plan view of another embodiment of a diaper backsheet of the present invention.

In an alternative embodiment, shown in FIG. 4, layer 250 is preferably positioned adjacent to the absorbent core. FIG. 4 shows a plan view of the diaper backsheet 226 with the portion of the backsheet positioned adjacent to the absorbent core facing the viewer. In this embodiment, layers 250 and 252 together form the outer surface of the diaper. Layer 252 is the portion of the backsheet 226 which will prevent the exudates absorbed and contained in the absorbent core from wetting articles which contact the diaper. In order to provide additional comfort for the wearer, layer 252 is preferably breathable. To this end, layer 252 should exhibit substantially zero dynamic fluid transmission when subjected to an impact energy of about 1000 joules/$m^2$ and a mass vapor transmission rate of at least about 2000 $g/m^2/24$ hr. Preferably, layer 252 while exhibiting a mass vapor transmission rate of at least about 2000 $g/m^2/24$ hr. will also exhibit substantially zero dynamic fluid transmission when subjected to impact energies of about 2000 joules/$m^2$, about 3000 joules/$m^2$, and about 4000 joules/$m^2$. The outermost layer 252 may exhibit substantially zero dynamic fluid transmission when subjected to even higher impact energies, e.g., impact energies of at least about 5000 joules/$m^2$ or greater.

In order to protect the user against unwanted leakage, layer 252 should have width and length dimensions larger than that of the absorbent core. If layer 252 is not large enough, exudates absorbed and contained in the absorbent core could be forced through the nonwoven layer 250 during normal usage conditions. Therefore, the layer 252 should at least have length and width dimensions larger than that of the absorbent core and if desired may form portions of the side edges and end edges of the diaper.

In an alternative embodiment, a breathable nonwoven/film laminate backsheet can be made suitable, such that a portion of the backsheet, (the portion directly behind the absorbent core), contains the fluid impervious, non-breathable portion while the outer or side portions of the backsheet, (the portions of the backsheet which extend beyond the absorbent core), contain the breathable portion.

Figure 5:
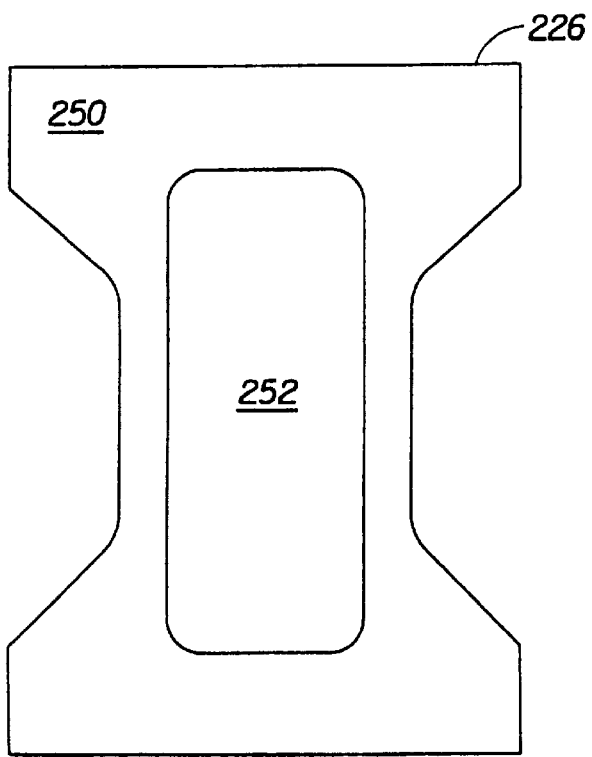
FIG. 5 is a plan view of another embodiment of a diaper backsheet of the present invention.

In this embodiment, shown in FIG. 5 with the portion of the backsheet 226 positioned adjacent to the absorbent core facing the viewer, layer 250 forms the outer surface of the diaper and layer 252 is positioned adjacent to the absorbent core. Since layer 250 is that portion of the backsheet 226 which will come into contact with the wearer's skin, layer 250 is preferably soft and comprises a nonwoven web. In addition to being soft, layer 250 is also breathable. Layer 250 preferably exhibits a mass vapor transmission rate of at least about 2000 $g/m^2/24$ hr., more preferably at least about 2500 $g/m^2/24$ hr., and most preferably at least about 3000 $g/m^2/24$ hr. Layer 250 may have a higher mass vapor transmission rate, e.g., mass vapor transmission rate of at least about 4000 $g/m^2/24$ hr. or greater.

Layer 252 is the portion of the backsheet 226 which will prevent the exudates absorbed and contained in the absorbent core from wetting articles which contact the diaper. Layer 252 need not be breathable, as this function is provided by layer 252. To this end, layer 252 should exhibit substantially zero dynamic fluid transmission when subjected to an impact energy of about 1000 joules/m$^2$. Preferably, layer 252 will also exhibit substantially zero dynamic fluid transmission when subjected to impact energies of about 2000 joules/m$^2$, about 3000 joules/m$^2$, and about 4000 joule/m$^2$. The innermost layer 252 may exhibit substantially zero dynamic fluid transmission when subjected to even higher impact energies, e.g., impact energies of at least about 5000 joules/m$^2$ or greater.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article, comprising:
    a backsheet at least a portion of which is extensible and at least a portion of which exhibits substantially zero dynamic fluid transmission when subjected to an impact energy of about 1000 joules/m$^2$, and a mass vapor transmission rate of at least about 2000 g/m$^2$/24 hr.
    a fluid pervious topsheet secured to said backsheet; and
    an absorbent core positioned between said topsheet and said backsheet.

2. The disposable absorbent article of claim 1 wherein said portion of said backsheet which exhibits substantially zero dynamic fluid transmission when subjected to an impact energy of about 1000 joules/m$^2$, and a mass vapor transmission rate of at least about 2000 g/m$^2$/24 hr., comprises an extensible portion of said backsheet.

3. The disposable absorbent article of claim 1 wherein an extensible portion of said backsheet comprises a material which has been incrementally mechanically stretched.

4. The disposable absorbent article of claim 1 wherein an extensible portion of said backsheet comprises a web material including:
    a pair of first regions each having a first axis in a first direction and a surface-pathlength measured generally parallel to a first axis while said material is in an untensioned condition;
    a second region disposed between said first regions, said second region including one or more raised rib-like elements having an axis substantially perpendicular to said first axis and having surface-pathlength which is greater than that of said first regions as measured substantially parallel to said first axis while said material is in an untensioned condition; and
    a transitional region at the interface between each said first region and said second region.

5. The disposable absorbent article of claim 1 wherein an extensible portion of said backsheet consists of a single layer.

6. The disposable absorbent article of claim 5 wherein said single layer of said backsheet has been incrementally mechanically stretched.

7. The disposable absorbent article of claim 5 wherein said single layer of said backsheet comprises a web material including:
    a pair of first regions each having a first axis in a first direction and a surface-pathlength measured generally parallel to a first axis while said material is in an untensioned condition;
    a second region disposed between said first regions, said second region including one or more raised rib-like elements having an axis substantially perpendicular to said first axis and having surface-pathlength which is greater than that of said first regions as measured substantially parallel to said first axis while said material is in an untensioned condition; and
    a transitional region at the interface between each said first region and said second region.

8. The disposable absorbent article of claim 1 wherein said backsheet comprises at least two layers joined together.

9. The disposable absorbent article of claim 8 wherein at least one of said at least two layers of said backsheet has been incrementally mechanically stretched.

10. The disposable absorbent article of claim 8 wherein said at least one of said at least two layers of said backsheet comprises a web material including:
    a pair of first regions each having a first axis in a first direction and a surface-pathlength measured generally parallel to a first axis while said material is in an untensioned condition;
    a second region disposed between said first regions, said second region including one or more raised rib-like elements having an axis substantially perpendicular to said first axis and having surface-pathlength which is greater than that of said first regions as measured substantially parallel to said first axis while said material is in an untensioned condition; and
    a transitional region at the interface between each said first region and said second region.

11. The disposable absorbent article of claim 1 wherein an extensible portion of said backsheet comprises a film extrusion coated onto a nonwoven web.

12. The disposable absorbent article of claim 11 wherein said extrusion coated nonwoven web is elastically extensible.

13. The disposable absorbent article of claim 11 wherein said extrusion coated nonwoven web has been incrementally mechanically stretched.

14. The disposable absorbent article of claim 11 wherein said extrusion coated nonwoven web comprises a web material including:
    a pair of first regions each having a first axis in a first direction and a surface-pathlength measured generally parallel to a first axis while said material is in an untensioned condition;
    a second region disposed between said first regions, said second region including one or more raised rib-like elements having an axis substantially perpendicular to said first axis and having surface-pathlength which is greater than that of said first regions as measured substantially parallel to said first axis while said material is in an untensioned condition; and
    a transitional region at the interface between each said first region and said second region.

15. The disposable absorbent article of claim 1 wherein said article comprises a rear waist region and an extensible portion of said backsheet is located in said rear waist region.

16. The disposable absorbent article of claim 15 wherein said absorbent core is not joined to said backsheet in said rear waist region.

17. The disposable absorbent article of claim 15 wherein said extensible portion located in said rear waist region is elastically extensible.

18. The disposable absorbent article of claim 17 wherein said absorbent core is not joined to said backsheet in said rear waist region.

19. The disposable absorbent article of claim 1 wherein said article comprises a front waist region and where an extensible portion of said backsheet is located in said front waist region.

20. The disposable absorbent article of claim 19 wherein said absorbent core is not joined to said backsheet in said front waist region.

21. The disposable absorbent article of claim 19 said extensible portion located in said front waist region is elastically extensible.

22. The disposable absorbent article of claim 21 wherein said absorbent core is not joined to said backsheet in said front waist region.

23. The disposable absorbent article of claim 1 wherein said backsheet exhibits a mass vapor transmission rate of at least about 3000 g/m$^2$/24 hr in an extensible portion of said backsheet.

24. The disposable absorbent article of claim 1 wherein said backsheet exhibits substantially zero dynamic fluid transmission when subjected to an impact energy of about 3000 joules/m$^2$, and a mass vapor transmission rate of at least about 2000 g/m$^2$/24 hr in an extensible portion of said backsheet.

25. The disposable absorbent article of claim 1 wherein said backsheet exhibits substantially zero dynamic fluid transmission when subjected to an impact energy of about 3000 joules/m$^2$, and a mass vapor transmission rate of at least about 2000 g/m$^2$/24 hr in an elastically extensible portion of said backsheet.

26. The disposable absorbent article of claim 1 wherein said backsheet exhibits substantially zero dynamic fluid transmission when subjected to an impact energy of about 4000 joules/m$^2$, and a mass vapor transmission rate of at least about 2000 g/m$^2$/24 hr in an extensible portion of said backsheet.

27. The disposable absorbent article of claim 1 wherein said backsheet exhibits substantially zero dynamic fluid transmission when subjected to an impact energy of about 4000 joules/m$^2$, and a mass vapor transmission rate of at least about 2000 g/m$^2$/24 hr in an elastically extensible portion of said backsheet.

* * * * *

UNITED STATES PATENT AND TRADEMARK OFFICE
CERTIFICATE OF CORRECTION

PATENT NO. : 6,198,018 B1
DATED : March 6, 2001
INVENTOR(S) : John J. Curro

It is certified that error appears in the above-identified patent and that said Letters Patent is hereby corrected as shown below:

<u>Column 2,</u>
Line 65, delete "it" and insert therefore -- a --.

<u>Column 3,</u>
Line 45, delete "this" and insert therefor -- the --.

<u>Column 4,</u>
Line 16, delete "front" and insert therefor -- from --.

<u>Column 7,</u>
Line 65, delete "Saint Paul, Minn." and insert therefor -- St. Paul, Minn. --.
Line 65, after "Saint Paul, Minn." insert a line break and a carriage return.

<u>Column 8,</u>
Line 22, delete "2000 /m$^2$/24 hr." and insert therefore -- 2000 g/m$^2$/24 hr --.
Line 37, after "preferably" delete "-" (the hyphen).

<u>Column 9,</u>
Line 2, delete "All" and insert therefor -- As --.

<u>Column 10,</u>
Line 4, after "films" delete "," (one of the commas).
Line 41, after "described" delete "." (the period).
Line 46, after "No" insert therefor -- . -- (a period).
Line 67, after "initially" delete ")" (the right parenthesis).

UNITED STATES PATENT AND TRADEMARK OFFICE
CERTIFICATE OF CORRECTION

PATENT NO.    : 6,198,018 B1
DATED         : March 6, 2001
INVENTOR(S)   : John J. Curro It is certified that error appears in the above-identified patent and that said Letters Patent is hereby corrected as shown below:

Column 13,
Line 4, after "No" delete ":" (the colon) and insert therefore -- . -- (the period).
Line 8, delete "Battrelt" and insert therefore -- Battrell --.

Signed and Sealed this

Twenty-second Day of October, 2002

Attest:

JAMES E. ROGAN
Attesting Officer    Director of the United States Patent and Trademark Office